(12) United States Patent
Charles-Lundaahl

(10) Patent No.: US 6,623,467 B1
(45) Date of Patent: Sep. 23, 2003

(54) REUSABLE DIAPER

(76) Inventor: Lotta Charles-Lundaahl, Box 120, Burton, British Columbia, V0G 1E0 (CA)

( * ) Notice: Subject to any disclaimer, the term of this patent is extended or adjusted under 35 U.S.C. 154(b) by 506 days.

(21) Appl. No.: 09/686,853

(22) Filed: Oct. 12, 2000

Related U.S. Application Data

(60) Provisional application No. 60/159,206, filed on Oct. 13, 1999.

(51) Int. Cl.[7] ............................................. A61F 13/15
(52) U.S. Cl. .................... 604/385.201; 604/385.01; 604/385.03; 604/385.16; 604/385.18; 604/385.23; 604/385.29; 604/385.3
(58) Field of Search .................. 404/385.01, 385.03, 404/385.101, 385.16, 385.18, 385.201, 385.23, 385.25, 385.29, 385.3, 386; 2/400, 401, 403, 406

(56) References Cited

U.S. PATENT DOCUMENTS 5,685,873 A * 11/1997 Bruemmer ............. 604/385.24
6,004,306 A * 12/1999 Robles et al. .......... 604/385.21
6,093,422 A * 7/2000 Denkewicz et al. ........ 424/618
6,217,780 B1 * 4/2001 Denkewicz et al. ........ 210/764

FOREIGN PATENT DOCUMENTS

CA          2323248 A1 *  4/2001    ........... A61F/13/49

* cited by examiner

*Primary Examiner*—John J. Calvert
*Assistant Examiner*—Angela J Grayson
(74) *Attorney, Agent, or Firm*—Antony C. Edwards

(57) ABSTRACT

A reusable diaper is made of two sheets of fabric. One sheet is an absorbant rectangular sheet. The second sheet is an inverted bell-shape and may be of resilient material. The absorbant sheet is stitched along one edge to the bell-shaped sheet along the length of the axis of symmetry of the bell-shaped sheet. The absorbant sheet is only stitched to the bell-shaped sheet adjacent one corner of the absorbant sheet so that, when unfolded, the absorbant sheet is at least twice the length of the axis of symmetry of the bell-shaped sheet. The absorbant sheet may thus be folded into a narrow rectangular absorbant pad lying along the axis of symmetry of the bell-shaped sheet. The opposite tapered ends of the bell-shaped sheet are wrapped around an infant's waist and are drawn to the front of the infant through a loop on the vertex of the bell-shape once the vertex has pulled lifted up between the infant's legs.

8 Claims, 4 Drawing Sheets

REUSABLE DIAPER

CROSS REFERENCE TO RELATED APPLICATION

This application claims priority from U.S. Provisional Patent Application No. 60/159,206 filed Oct. 13, 1999 titled REUSABLE DIAPER.

FIELD OF THE INVENTION

This invention relates to the field of diapers and in particular to reusable diapers made of cloth where the diaper fastener is formed of the diaper material itself.

BACKGROUND OF THE INVENTION

Many designs of reusable diapers have been proposed in the prior art. In this disclosure, the field has been narrowed by eliminating reference to those prior art diapers requiring various forms of fasteners such as safety pins, straps and buckles, snaps, zippers, and hook and loop pile fasteners such as sold under the Trademark Velcro. This background disclosure is restricted to those prior art diaper designs using either tie strings or the diaper material itself to fasten the diaper about the body of an infant.

In particular, Applicant is aware of U.S. Pat. No. 2,898,912 which issued Aug. 11, 1959 to Adams for an Infant's Diaper. Adams discloses diaper material cut into an hourglass shape. Tabs extend laterally from the widest portion of the material which forms the back of the diaper. A pocket is formed on the inner face of the diaper for holding an absorbent pad. Slits in the front face of the front portion receive the tabs once wrapped around the sides of the infant. The pair of tabs are inserted in opposed facing relationship through a pair of corresponding slits, and the tabs pulled through the opposite slit so as to tighten the diaper around the waist of the infant.

Applicant is also aware of Canadian patent No. 491,088 which issued Mar. 10, 1953 to Ward. Ward also discloses the use of an hourglass-shaped sheet of diaper material. Lengths of tape extend laterally from the corners of the sheet. Once fitted onto an infant, the lengths of tape are wrapped around the waist of the infant and secured by tying. Cooperating slits provide for sliding one opposed pair of tape ends through the slits so as to bring the tape ends to the front of the diaper for tying. The other pair of oppositely disposed tape ends are wrapped around the waist so as to bring the tape ends to the rear of the diaper. One of the tape ends is then threaded through a fixed loop and the tape ends then tied.

U.S. Pat. No. 2,570,963 which issued to Mesmer on Oct. 9, 1951 for an Infant's Diaper, teaches a sheet of diaper material having three laterally adjacent sections. Each section of the three sections has a pair of slits in the upper opposite corners of the section so that folding the two outermost sections over onto the inner section aligns the three pairs of slits. The sheet is cut so as to define a generally oppositely disposed pair of tie strings depending downwardly from the outermost sections so that when the outermost sections are folded over onto the inner section, the tie strings criss-cross. The upper folded over portions of the sections, that is, the upper portion of the diaper having the aligned pairs of slits, forms the back of the diaper. The tie strings are pulled up between an infant's legs so that the ends of the tie strings lay generally diagonally across the infant's waist. The ends of the tie strings may then be wrapped around the infant's waist and journalled through the aligned pairs of slits. The ends of the tie strings may then be tied by means of a single loop or knot to secure the front of the diaper to the back of the diaper.

Canadian patent No. 450,197 which issued Aug. 3, 1948 to Grogan for a Diaper Protector discloses, instead of the use of separate rubber pants to cover a diaper, a plastic cloth protector upon which a diaper folded in oblong form may be placed and the two elements secured on the child at the same time. Once again it is taught to use an hourglass shape, and ties formed of tape extending laterally oppositely from two oppositely disposed corners of the sheet, the portion of the diaper therebetween forming the back of the diaper. The opposite end of the hourglass shape is brought up between the legs of the child to form the front of the diaper and the corresponding corners of both ends of the hourglass shape are pinned together. The ties are brought around the waist of the child and tied at the front of the diaper.

Canadian patent No. 420,310 which issued on May 23, 1944 to Herscovici for a Diaper also teaches the use of folding a pre-formed sheet of diaper material so as to bring one end of the sheet up between the legs of an infant and securing the opposite corners of the sheet to one another by passing lengths of tape through corresponding openings and fastening by tying.

Canadian patent No. 413,607 which issued Jul. 6, 1943 to Brown for a Diaper discloses folding a rectangular sheet of diaper material so as to position ties extending laterally from the rectangle with corresponding openings along the sides of the rectangle so that, once folded and one end passed up between the legs of an infant, one end of the rectangle may be secured to the front of the infant by passing the ties from the back of the diaper around the waist of the infant so as to secure the front to the back by tying the ties through the openings.

Canadian patent No. 412,533 which issued May 18, 1943 to Sonnenberg for a Diaper similarly teaches the use of ties extending laterally from a rectangular sheet of diaper material so that once folded to form leg openings, the ties may be secured around the waist of the infant, the ends of the ties cooperating with loops formed on oppositely disposed lateral sheet extensions formed at one end of the rectangle.

Lastly, applicant is also aware of U.S. Pat. No. 1,649,958 which issued Nov. 22, 1927 to Hoyme for a Diaper. Hoyme teaches the use of a rectangle of diaper material which is folded into a triangle. One corner of the rectangle is slitted so as to form elongate cloths bands which, once the material is folded into the triangle, extend from opposite corners of the triangle. The oppositely disposed bands extending from the opposite corners of the triangle may be passed around the waist of an infant so as to engage loops in the remaining corner of the triangle, that is, the triangle vertice, which has been brought up between the legs of the infant. The bands are threaded through the loops and tied together to fasten the diaper onto the infant.

None of these prior art diaper designs exhibit the advantages of the reusable diapers of the present invention as better described below.

SUMMARY OF THE INVENTION

In summary, the reusable diaper of the present invention includes flexible first and second sheets, where the first sheet is a sheet of absorbent fabric and the second sheet is a sheet of fabric having only three corners. The corners of the second sheet are generally equally radially spaced about a center of a mid-portion the second sheet. A first corner forms a vertex. The second and third corners form oppositely disposed elongate first and second ends. An axis of symmetry of the second sheet bisects the mid-portion between the first and second ends so as to intersect the vertex.

A first end, or other portion of the first sheet is mounted to a first surface of the second sheet substantially along the axis of symmetry of the second sheet. With the first sheet so mounted to the second sheet, and with both the first and second sheets laid flat and unfolded, a second end of the first sheet opposite the first end extends from the vertex of the second sheet sufficiently so that when the first sheet is folded about a first fold line perpendicular to the axis of symmetry, the second end of the first sheet overlays the first end of the first sheet.

The first sheet extends from the axis of symmetry of the second sheet sufficiently so that the first sheet may be folded about a second fold line parallel to, for example spaced from, the axis of symmetry so that, when a first side edge of the first sheet, is folded about the second fold line, the first side edge of the first sheet overlays an opposite side of the first sheet, for example adjacent an opposite second side edge. At least one loop is mounted to a second surface of the second sheet, opposite the first surface, along the axis of symmetry adjacent the vertex. The loop is sized so as to receive the first and seconds ends of the second sheet therethrough.

In one aspect of the present invention the first sheet may be a parallelogram, advantageously rectangular, although this is not intended to be limiting, the scope of the present invention intended to include other shapes, for example other polygons such as octagons. Further, the second sheet may be bell-shaped and resilient, with the vertex being a vertex of the bell-shape.

Where the first fold line is a first lateral fold line, and the second fold line is a first longitudinal fold line, the first sheet is advantageously sufficiently large so that:

(a) when folded about the first lateral fold line and subsequently folded again about at least one further lateral fold line parallel to the first lateral fold line, and (b) when folded about the first longitudinal fold line and subsequently folded again about at least one further longitudinal fold line parallel to the first longitudinal fold line, the first sheet forms a substantially rectangular absorbent pad extending from a waistband edge of the second sheet, where the waistband edge is between the first and second ends of the second sheet, along the axis of symmetry so as to extend to at least the vertex of the second sheet.

In yet a further aspect, the first and second ends of the second sheet are sufficiently elongate so that, when the vertex has been folded over onto the mid-portion so that the edges of the bell-shape between the first and second ends and the vertex define leg-receiving loops for wrapping around the thighs of an infant, the first and second ends may be passed in opposite directions through one loop of the linear array of loops and gently pulled oppositely sufficiently through the loop to:

(a) snug the waistband edge of the second sheet around the waist of the infant, and (b) allow tying of the first and second ends to one another.

DETAILED DESCRIPTION OF PREFERRED EMBODIMENTS

Figure 1:
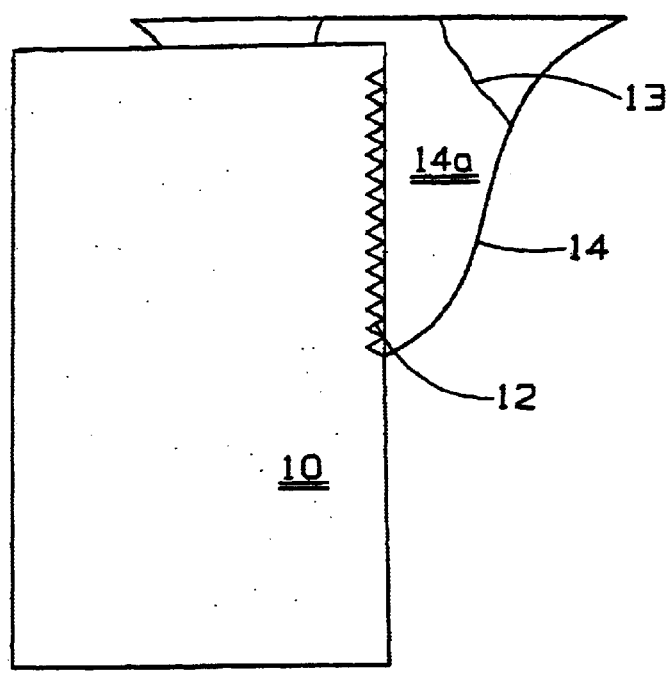
FIG. 1 is, in top plan view, the reusable diaper of the present invention unfolded and laid flat.
Figure 2:
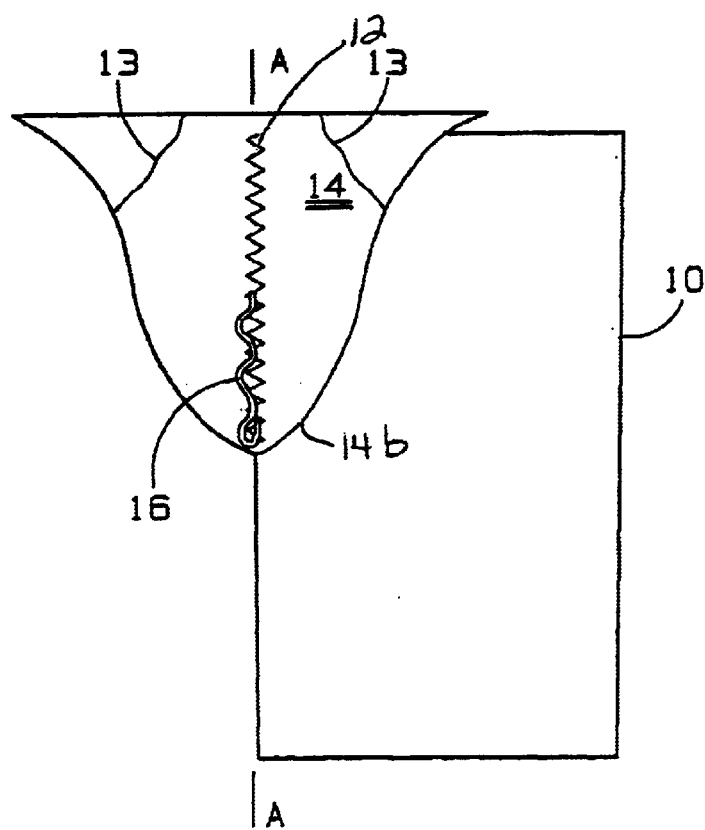
FIG. 2 is, in bottom plan view, the reusable diaper of FIG. 1.
Figure 1A:
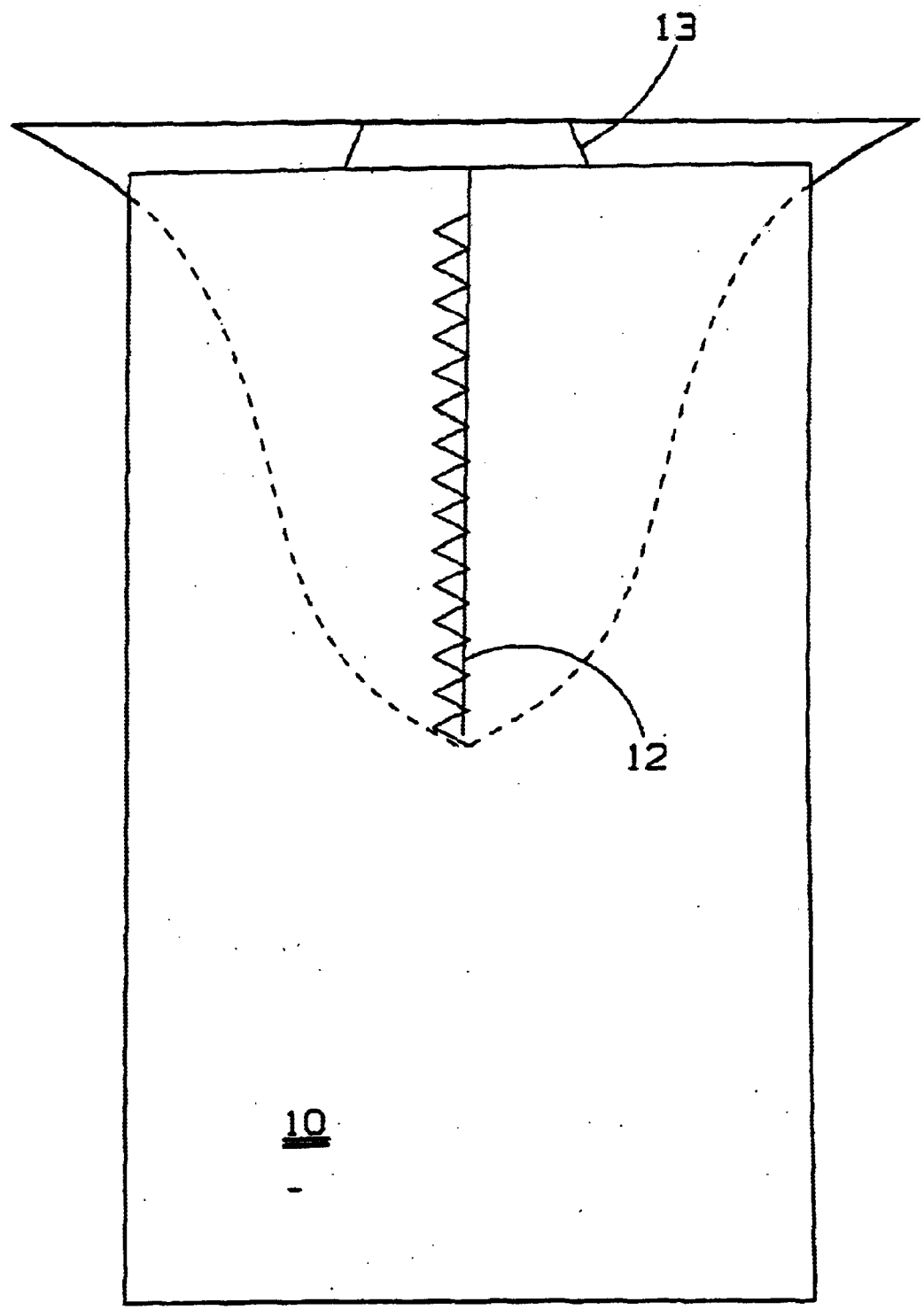
FIG. 1a is an alternative embodiment of the reusable diaper of the present invention.

As seen in FIGS. 1 and 2, the reusable diaper of the present invention has two material components, namely a single layered sheet 10 fastened as by stitching along seam 12 to single layer stretch fabric 14. Stretch fabric sheet 14 is formed as an inverted bell shape. Sheet 10 is generally rectangular and is of absorbent fabric. Seam 12 runs along approximately ½ of the length of one lateral side edge of sheet 10 so as to mount sheet 10 by means of seam 12 along axis of symmetry A of stretch fabric sheet 14. In the alternative embodiment of FIG. 1a, seam 12 bisects sheet 10. The illustrated positions of seam 12 on sheet 10 are not intended to be limiting, so long as sheet 10 may be folded into an absorbent pad, for example in the manner described below.

Sheet 14 may comprise a midportion containing seam 12, and oppositely disposed elongate ends mounted to the midportion along gathered seams 13. Seams 13 advantageously gather the corresponding edges of the midportion so as to cup sheet 10 in the concavity formed by the pair of seams 13 on either side of seams 12.

Seam 12 extends along an inner surface 14a of stretch fabric sheet 14. Cotton cord loops 16 are mounted to the opposite side, that is the outer surface, of stretch fabric sheet 14 also along axis of symmetry A towards the vertex-like end 14b of the bell shape.

Figure 4:
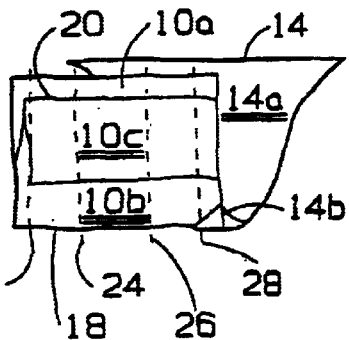
FIG. 4 is the reusable diaper of FIG. 3 folded along the lateral fold lines.
Figure 5:
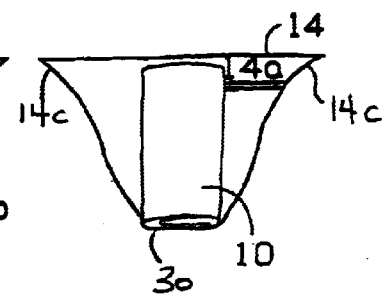
FIG. 5 is the reusable diaper of FIG. 4 folded along the longitudinal fold lines.
Figure 9:
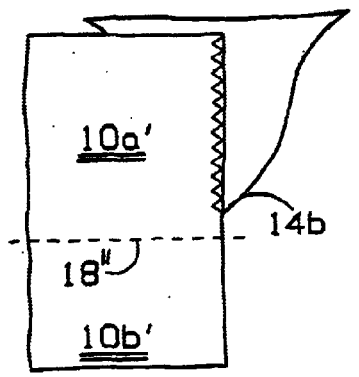
FIG. 9 is the view of FIG. 1 illustrating the fold line pattern for a large size fit.
Figure 10:
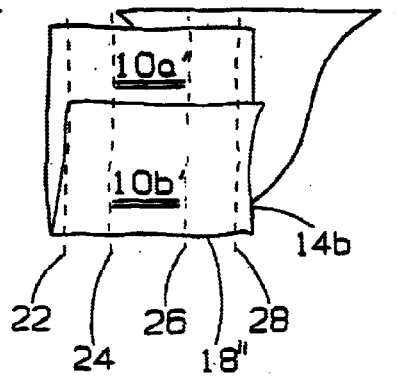
FIG. 10 is the reusable diaper of FIG. 9 folded along the lateral fold lines.
Figure 11:
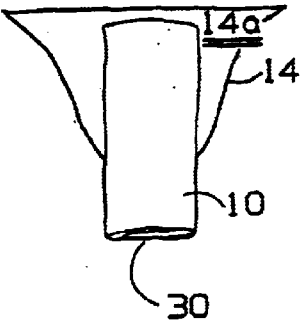
FIG. 11 is the reusable diaper of FIG. 10 folded along the longitudinal fold lines.

What follows is a description of the method of folding sheet 10 so as to accommodate different sizes of infant. For sake of convenience and clarity, FIGS. 3–5 are directed to fitting a small infant, FIGS. 6–8 are directed to fitting a medium-sized infant, and FIGS. 9–11 are directed to fitting a large-sized infant, it being understood that with suitable adjustments in the folding that any size of infant generally between 7 and 50 pounds may be accommodated.

Figure 3:
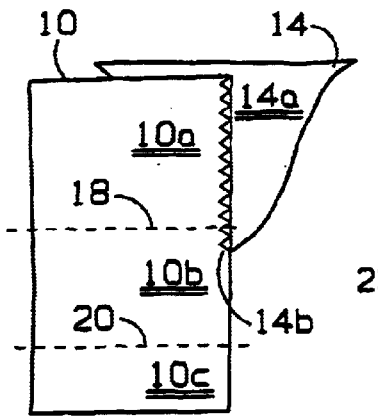
FIG. 3 is the view of FIG. 1 illustrating the fold line pattern for a small size fit.

Thus in FIG. 3 sheet 10 is divided into three portions, 10a, 10b and 10c, by lateral fold lines 18 and 20, respectively. Sheet 10 may be folded over on itself on fold lines 18 and 20 in a Z-pattern in the manner illustrated in FIG. 4 noting that for this small size that fold line 18 crosses surface 14a of stretch fabric sheet 14 adjacent or spaced from vertex 14b so that, as seen in FIG. 4, the fold along fold line 18 also folds vertex 14b back over onto surface 14a.

Fold lines 18 and 20 are laterally extending fold lines extending between the laterally spaced apart side edges of sheet 10. In order to result in the absorbent pad seen in FIG. 5, sheet 10 once folded into the configuration seen in FIG. 4, is also further folded along longitudinally extending fold lines 22, 24, 26 and 28. The result is the generally rectangular folded over shape seen in FIG. 5 once sheet 10 in the configuration of FIG. 4 is folded sequentially over on itself starting along fold line 22 and proceeding then to fold along fold lines 24, 26 and 28 sequentially.

Figure 6:
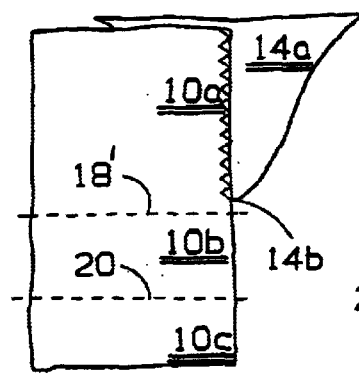
FIG. 6 is the view of FIG. 1 illustrating the fold line pattern for a medium size fit.
Figure 7:
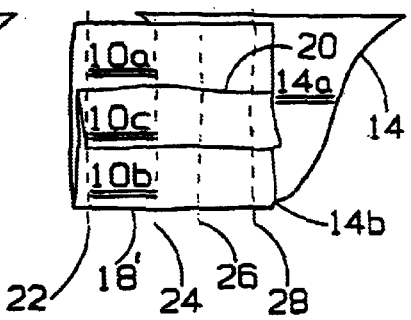
FIG. 7 is the reusable diaper of FIG. 6 folded along the lateral fold lines.
Figure 8:
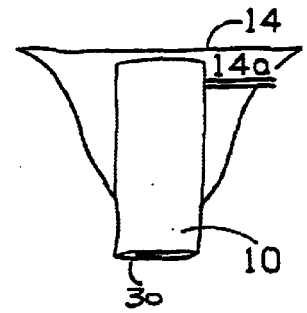
FIG. 8 is the reusable diaper of FIG. 7 folded along the longitudinal fold lines.

The placement of the fold lines in FIGS. 6–8 are adjusted to accommodate a larger, that is, medium sized infant. Thus fold line 18' is shifted (relative to fold line 18 in FIG. 3) so as not to cross surface 14a, rather, crossing axis of symmetry A adjacently spaced from vertex 14b. This movement of fold line 18' provides for a longer rectangular shape of absorbent pad as seen in FIG. 8. Again, longitudinally extending fold lines 22, 24, 26 and 28 are used sequentially to fold sheet 10 into the absorbent pad.

Similarly, in FIGS. 9–11, the laterally extending fold lines are adjusted so as to provide the long rectangular absorbent pad of FIG. 11 so as to fit a larger sized infant. Fold line 18" is spaced further from vertex 14b (as compared to fold line 18' in FIG. 7) and fold line 20 is left out entirely. Thus sheet 10 is only folded about one laterally extending fold line so as to partition sheet 10 into only two sections 10a' and 10b'. With section 10b' folded over onto section 10a' about fold line 18", sheet 10 may then be folded, as before, sequentially about longitudinally extending fold lines 22, 24, 26 and 28 so as to result in the elongate absorbent pad of FIG. 11.

Figure 12:
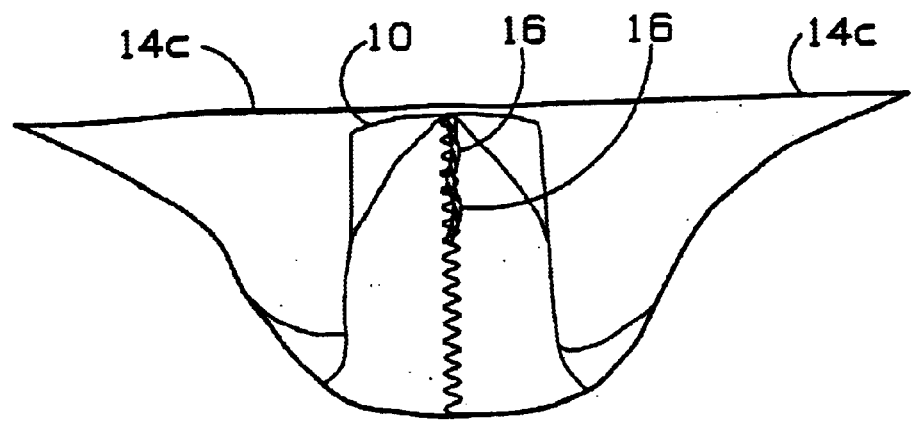
FIG. 12 is, in plan view, the reusable diaper of FIG. 8 folded to fold the absorbent pad over the abdomen of an infant.

Once sheet 10 has been folded into the appropriate size suited for the size of the infant, and stretch fabric sheet 14 has been laid flat to thereby upwardly centrally dispose the now folded sheet 10 formed as an absorbent pad, the infant (not shown) is laid so as to place the back of the infant onto the upper edge of sheet 14. This positions the infant's bottom intermediate along the absorbent pad. End 30 of the absorbent pad is then brought up between the legs of the infant so as to fold end 30 over the abdomen of the infant. This presents loops 16 on the front of the diaper as seen in FIG. 12.

Figure 13:
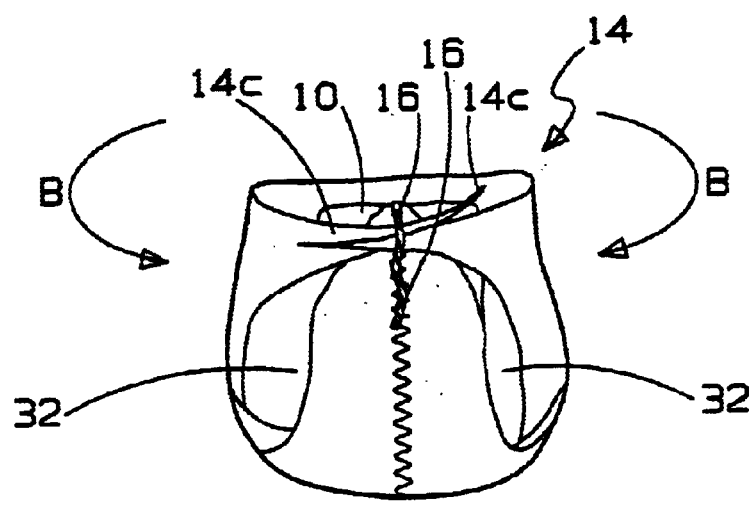
FIG. 13 is the diaper of FIG. 12 with the laterally outermost ends of the diaper folded over so as to tighten the diaper waist band and so as to secure the absorbent pad.
Figure 14:
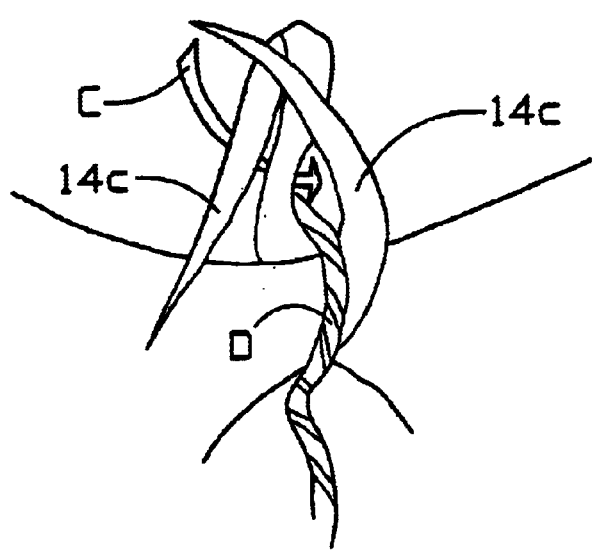
FIG. 14 illustrates, in partially cutaway enlarged view, how the ends of the diaper waist band may be tied.

As seen in FIG. 13, ends 14c of sheet 14 are then rotated in directions B around the waist of the infant and across the front of the infant so as to be threaded through one of loops 16. Ends 14c may then be gently pulled in opposite directions so as to snug sheet 14 around the waist of the infant thereby also snugging the perimeter edges of leg apertures 32 around the infant's thighs. The oppositely disposed ends 14c protruding through loop 16 may then be knotted as, for example, illustrated in FIG. 14, by passing one end in direction C around the other end formed into a loop. This releasably secures sheet 14 around the infant thereby securing sheet 10 positioned for optimum absorbency. In choosing which loop 16 to use to secure ends 14c, a loop is chosen which best snugly fits sheet 10 in its folded form up underneath the crotch of the infant, that is, that loop which provides the best fit.

Thus as may be seen, the reusable diaper of the present invention provides for simplicity of manufacture using two sheet single layer construction, such simplicity lending to ease of maintenance, ease of laundering including short drying time of the two single sheets. The simple folding method of the present invention also provides for a stepless sizing for superior fit without the need for releasable fasteners such as known in the prior art including pins, hook and loop fasteners, snaps, zippers or the like which are generally inconvenient, wear out and add to manufacturing costs.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A reusable diaper comprising: flexible first and second sheets, said first sheet of absorbent fabric, said second sheet formed of fabric having only three corners, said corners generally equally radially spaced about a center of a mid-portion said second sheet, a first corner of said three corners forming a vertex, second and third corners of said three corners forming oppositely disposed elongate first and second ends, an axis of symmetry of said second sheet bisecting said mid-portion between said first and second ends of said second sheet so as to intersect said vertex, said first sheet mounted to a first surface of said second sheet substantially along said axis of symmetry so that, with said first sheet mounted to said second sheet and both said first and second sheets laid flat and unfolded, an end of said first sheet extends from said vertex of said second sheet sufficiently so that when said first sheet is folded about a first fold line perpendicular to said axis of symmetry, said end of said first sheet overlays an opposite end of said first sheet, said first sheet extending from said axis of symmetry sufficiently so that said first sheet may be folded about a second fold line parallel to, said axis of symmetry so that when a first side edge of said first sheet is folded about said second fold line, said first side edge of said first sheet overlays an opposite side of said first sheet, at least one loop mounted to a second surface of said second sheet, opposite said first surface, along said axis of symmetry adjacent said vertex, said at least one loop sized so as to receive said first and seconds ends of said second sheet therethrough.

2. The diaper of claim 1 wherein said first sheet is a parallelogram.

3. The diaper of claim 2 wherein said first sheet is rectangular.

4. The diaper of claim 1 wherein said second sheet is bell-shaped.

5. The diaper of claim 1 wherein said second sheet is resilient.

6. The diaper of claim 3 wherein said first fold line is a first lateral fold line, and said second fold line is a first longitudinal fold line, and wherein said second sheet is bell-shaped, said vertex being a vertex of said bell-shape.

7. The diaper of claim 6 wherein said first sheet is sufficiently large so that:

(a) when folded about said first lateral fold line and subsequently folded again about at least one further lateral fold line parallel to said first lateral fold line, and (b) when folded about said first longitudinal fold line and subsequently folded again about at least one further longitudinal fold line parallel to said first longitudinal fold line, said first sheet forms a substantially rectangular absorbent pad extending from a waistband edge of said second sheet, said waistband edge between said first and second ends of said second sheet, along said axis of symmetry so as to extend to at least said vertex of said second sheet.

8. The diaper of claim 6 wherein said first and second ends of said second sheet are sufficiently elongate so that when passed in opposite directions through one loop of said at least one loop when said vertex has been folded over onto said mid-portion so that the edges of said bell-shape between said first and second ends and said vertex define leg-receiving loops for wrapping around the thighs of an infant, said first and second ends may be pulled oppositely sufficiently through said one loop to snug a waistband edge of said second sheet, said waistband edge extending between said first and second ends, around the waist of said infant, and to allow tying of said first and second ends to one another.

* * * * *